US 9,350,956 B2

(12) United States Patent
Quilter et al.

(10) Patent No.: US 9,350,956 B2
(45) Date of Patent: *May 24, 2016

(54) CAPTURING AND PROCESSING INSTANT DRUG TEST RESULTS USING A MOBILE DEVICE

(71) Applicant: Compliance Software, Inc., Salt Lake City, UT (US)

(72) Inventors: Eric J. Quilter, Park City, UT (US); James Steven Buckmiller, Salt Lake City, UT (US); Scott M. Clark, Cape Elizabeth, ME (US)

(73) Assignee: Compliance Software, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/482,271

(22) Filed: Sep. 10, 2014

(65) Prior Publication Data
US 2014/0375803 A1    Dec. 25, 2014

Related U.S. Application Data

(60) Division of application No. 14/383,867, filed on Sep. 8, 2014, now Pat. No. 9,094,493, which is a continuation-in-part of application No. PCT/US2012/039181, filed on May 23, 2012, which is
(Continued)

(51) Int. Cl.
*H04W 24/00* (2009.01)
*H04N 7/18* (2006.01)
(Continued)

(52) U.S. Cl.
CPC ......... *H04N 7/185* (2013.01); *G01N 35/00871* (2013.01); *G06K 9/00577* (2013.01);
(Continued)

(58) Field of Classification Search
CPC ..... H04W 24/00; H04W 24/02; H04W 24/04; H04W 24/06; H04W 24/08; H04W 24/10; H04W 8/24; H04W 8/245
USPC .......................... 455/418, 419, 420, 423, 417
See application file for complete search history.

(56) References Cited

U.S. PATENT DOCUMENTS

| D275,788 S | 10/1984 | Givner |
| D285,114 S | 8/1986 | Collister |

(Continued)

FOREIGN PATENT DOCUMENTS

| CN | 1773288 | 11/2004 |
| DE | 102006019422 | 10/2007 |

(Continued)

OTHER PUBLICATIONS

International Search Report and Opinion, PCT/US2012/039181, Mailed Dec. 12, 2012.
(Continued)

*Primary Examiner* — Jean Gelin
(74) *Attorney, Agent, or Firm* — Workman Nydegger

(57) ABSTRACT

Systems, methods, and apparatus allow for capturing the results of drug tests using mobile devices. One or more implementations include apparatus that interface a mobile computing device with a drug test, while ensuring that an imaging device of the mobile computing device is optically aligned with a test display areas of the drug test. One or more additional implementations include a method for analyzing drug testing results. The method includes receiving and analyzing drug testing data, which includes an identification of a type drug testing apparatus being used at a remote testing device, and an image that visually represents a portion of a drug test. The method also includes analyzing the test results of the drug test based on the identification of the type drug testing apparatus.

8 Claims, 11 Drawing Sheets

Related U.S. Application Data a continuation of application No. 29/419,180, filed on Apr. 25, 2012, now Pat. No. Des. 701,320, and a continuation of application No. 29/419,182, filed on Apr. 25, 2012, now Pat. No. Des. 699,368.

(51) Int. Cl.
| | | |
|---|---|---|
| *G01N 35/00* | (2006.01) | |
| *G06K 9/00* | (2006.01) | |
| *H04N 5/222* | (2006.01) | |
| *H04M 1/725* | (2006.01) | |
| *H04W 24/06* | (2009.01) | |
| *H04W 24/08* | (2009.01) | |
| *H04M 1/02* | (2006.01) | |

(52) U.S. Cl.
CPC ......... *H04M1/72527* (2013.01); *H04N 5/2228* (2013.01); *G01N 2035/00108* (2013.01); *G06K 2009/0059* (2013.01); *G06K 2209/057* (2013.01); *H04M 1/0254* (2013.01); *H04W 24/06* (2013.01); *H04W 24/08* (2013.01)

(56) References Cited

U.S. PATENT DOCUMENTS

| | | | |
|---|---|---|---|
| 4,632,901 A | | 12/1986 | Valkirs |
| 5,289,378 A | | 2/1994 | Miller |
| D355,493 S | | 2/1995 | Gropper |
| D376,651 S | | 12/1996 | Paloian |
| 5,591,645 A | | 1/1997 | Rosenstein |
| 5,602,040 A | | 2/1997 | May |
| 6,376,251 B1 | * | 4/2002 | Braun ............. G01N 33/493 235/462.13 |
| D617,666 S | | 6/2010 | Stowers |
| D625,014 S | | 10/2010 | Hansen |
| D625,015 S | | 10/2010 | Hansen |
| D629,805 S | | 12/2010 | Nysen |
| D650,910 S | | 12/2011 | Shibata |
| D654,597 S | | 2/2012 | Hiramura |
| D661,309 S | | 6/2012 | Murrer |
| D661,810 S | | 6/2012 | Zanoni |
| D674,396 S | | 1/2013 | Yang |
| D682,432 S | | 5/2013 | Khan |
| D699,368 S | | 2/2014 | Quilter |
| D701,320 S | | 3/2014 | Quilter |
| 8,824,800 B2 | | 9/2014 | Bremnes |
| 9,094,493 B2 | | 7/2015 | Quilter |
| 2005/0106750 A1 | | 5/2005 | Tung |
| 2005/0191694 A1 | | 9/2005 | Jacobs |
| 2006/0073483 A1 | | 4/2006 | White |
| 2006/0074463 A1 | | 4/2006 | Seeberger |
| 2006/0177869 A1 | | 8/2006 | Heal |
| 2006/0222567 A1 | | 10/2006 | Kloepfer |
| 2006/0240453 A1 | | 10/2006 | Jacobs |
| 2006/0257956 A1 | | 11/2006 | Basset |
| 2006/0292040 A1 | | 12/2006 | Wickstead |
| 2007/0065339 A1 | | 3/2007 | Huff |
| 2007/0100397 A1 | | 5/2007 | Seeberger |
| 2008/0019867 A1 | | 1/2008 | Johnson |
| 2008/0194041 A1 | | 8/2008 | Guirguis |
| 2008/0228404 A1 | | 9/2008 | Garty |
| 2009/0132204 A1 | | 5/2009 | Bodlaender |
| 2009/0240115 A1 | | 9/2009 | Bluth |
| 2009/0240116 A1 | | 9/2009 | Bluth |
| 2009/0240524 A1 | | 9/2009 | Bluth |
| 2009/0240527 A1 | | 9/2009 | Bluth |
| 2009/0240528 A1 | | 9/2009 | Bluth |
| 2009/0240702 A1 | | 9/2009 | Bluth |
| 2009/0241177 A1 | | 9/2009 | Bluth |
| 2010/0049279 A1 | | 2/2010 | Seeberger |
| 2010/0152059 A1 | | 6/2010 | Zeichner |
| 2010/0173797 A1 | | 7/2010 | Jacobs |
| 2010/0263113 A1 | | 10/2010 | Shelton |
| 2011/0009163 A1 | | 1/2011 | Fletcher |
| 2011/0019883 A1 | | 1/2011 | Bremnes |
| 2011/0077469 A1 | | 3/2011 | Blocker |
| 2011/0144535 A1 | | 6/2011 | Guirguis |
| 2011/0176051 A1 | | 7/2011 | Randers-Pehrson |
| 2011/0257509 A1 | | 10/2011 | Olsen |
| 2011/0312531 A1 | | 12/2011 | Jacobs |
| 2012/0176498 A1 | * | 7/2012 | Haas ............. A61B 10/0045 348/148 |
| 2012/0203086 A1 | | 8/2012 | Rorabaugh |
| 2013/0053700 A1 | | 2/2013 | Ignotz |
| 2013/0209993 A1 | | 8/2013 | Aronowitz |
| 2014/0032406 A1 | * | 1/2014 | Roach ............. G06Q 20/042 705/42 |
| 2014/0234858 A1 | * | 8/2014 | Santagata ........ G01N 33/57484 435/7.1 |
| 2014/0296112 A1 | | 10/2014 | O'Driscoll |

FOREIGN PATENT DOCUMENTS

| | | |
|---|---|---|
| GB | 2483482 | 3/2012 |
| JP | 2008286522 | 11/2008 |
| WO | WO2010095394 | 8/2010 |
| WO | 2012032171 | 3/2012 |
| WO | WO2013162631 | 10/2013 |

OTHER PUBLICATIONS

Examiners Report—I5567 for application No. 2242-14.
European Search Report for EP 12875290 dated Oct. 23, 2015.

* cited by examiner

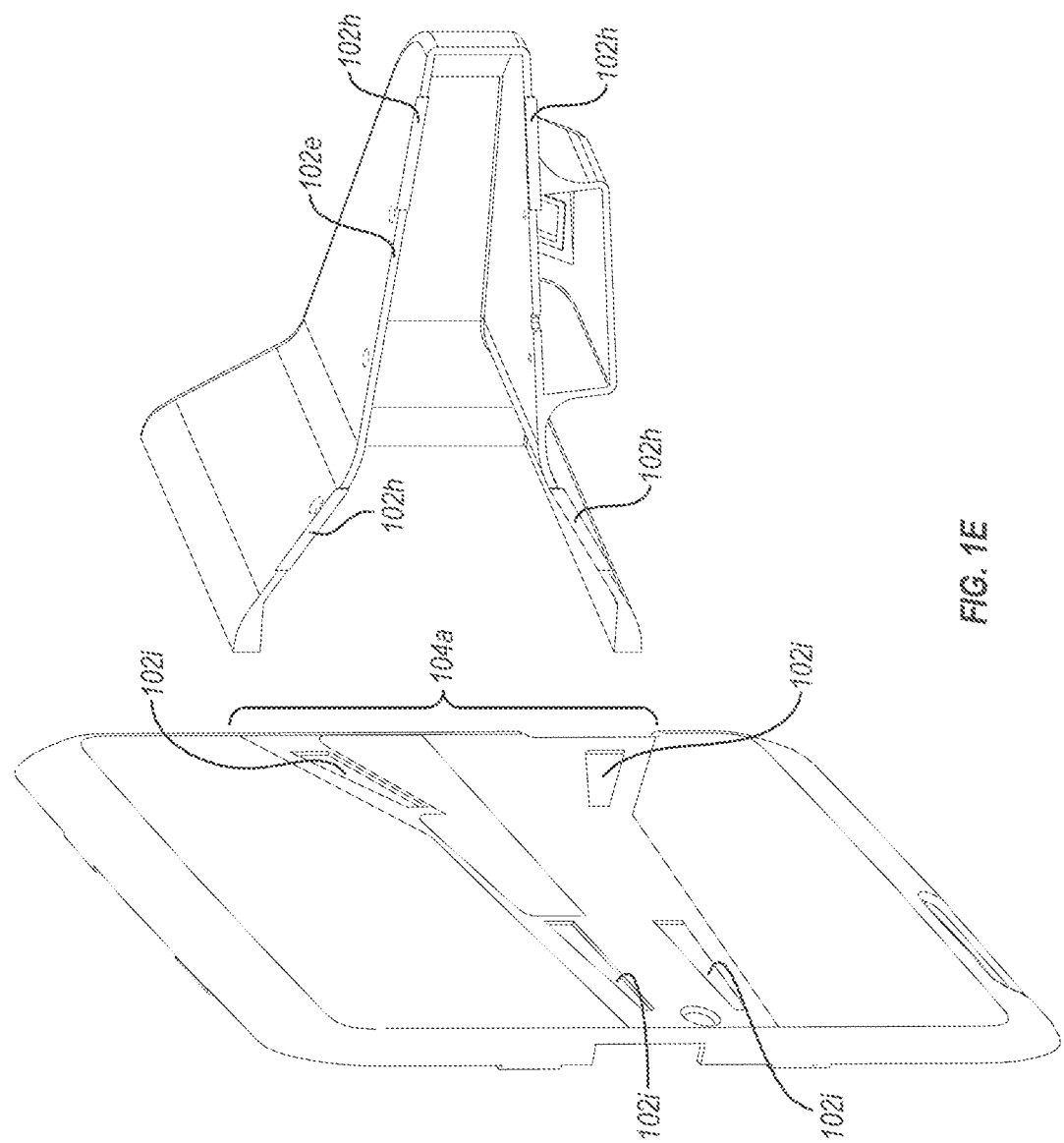

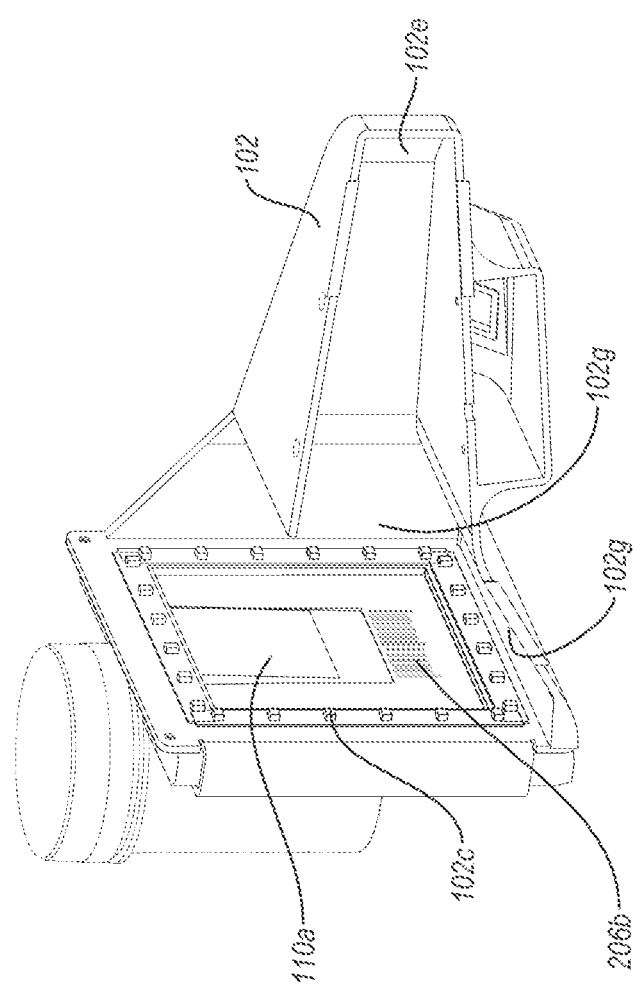

CAPTURING AND PROCESSING INSTANT DRUG TEST RESULTS USING A MOBILE DEVICE

CROSS-REFERENCE TO RELATED APPLICATIONS

The present invention is a Divisional of U.S. patent application Ser. No. 14/383,867, filed on Sep. 8, 2014, which is a 35 U.S.C. §371 U.S. National Stage of PCT Application No. PCT/US2012/039181 filed May 23, 2012, entitled "CAPTURING AND PROCESSING INSTANT DRUG TEST RESULTS USING A MOBILE DEVICE," which claims the benefit of and priority to U.S. Design patent application No. 29/419,180, filed Apr. 25, 2012, entitled "ADAPTABLE HOUSING FOR MOBILE DEVICE BASED DRUG TESTING," and now issued as U.S. Design Pat. No. D701,320, and U.S. Design patent application No. 29/419,182, filed Apr. 25, 2012, entitled "ADAPTABLE STAND FOR MOBILE BASED DRUG TESTING," now issued as U.S. Design Pat. No. D699,368. The entire content of each of the aforementioned patent applications is incorporated herein by reference.

BACKGROUND OF THE INVENTION

1. Field of the Invention

The present invention relates generally to apparatus and computer software for analyzing drug test results using mobile computing devices.

2. Background and Relevant Art

It is a common practice to test biological fluids (e.g., urine, saliva, blood, etc.) and/or tissues for the presence of particular chemicals, such as drugs, or chemicals that are indicative of a physiological state or medical condition (e.g., pregnancy, disease, etc.). For example, Point of Care Test (POCT) devices employ lateral flow testing, which is a form of immunoassay which provides a substrate along which a fluid test sample flows (e.g., via capillary action). Lateral flow test substrates generally include one or more testing areas (e.g., lines or zones) which are treated with one or more corresponding chemical reagents. As fluid test samples traverse testing areas on lateral flow test substrates, chemicals (e.g., drugs, proteins, etc.) in the test samples may react with the chemical reagent(s) in the testing areas. As part of the reaction(s) one or more colors of the testing areas may change or appear based on chemicals present in a particular test sample, thereby creating a visually readable result.

Test results produced by lateral flow tests used in POCT devices may be interpretable based on the presence of a color (or the lack thereof) in a test area, a combination colors in different test areas, differences between colors in different test areas, presence of lines, or a lack of lines, etc. As such, a human may, based on experience and/or comparison with a reference, interpret test results via a visual inspection of a lateral flow test substrate that has been exposed to a fluid test sample. Interpretation of results by a human; however, is prone to error. For example, different humans may perceive or differentiate colors differently, comparison of colors by humans is a subjective (rather than objective) process, humans may make errors when recording test results, etc. As such, the "human factor" can lead to inaccuracies in an otherwise reliable testing mechanism.

To overcome the "human factor" in lateral flow testing, entities that perform lateral flow testing increasingly employ computerized POCT readers. POCT readers use appropriate hardware (e.g., cameras, scanners, etc.) to acquire an image of lateral flow substrates, and perform a computerized analysis of the image to interpret the test areas and to generate a test result. As such, unlike humans, computerized POCT readers make an objective analysis of testing results, and record/report testing results without the introduction of transcription errors. Conventional POCT readers; however, can be prohibitive since conventional POCT readers are specifically configured to interpret results from specific POCT devices and their corresponding test(s). As such, if an entity needs to conduct a broad array of tests, it may be necessary to purchase a potentially large number of POCT devices (e.g., different POCT devices from different test manufacturers) and their corresponding POCT readers.

In addition to the foregoing, conventional POCT readers capture, analyze and produce results at the test site. This can lead to privacy issues. For example, a workers response to a test result can unintentionally inform other people at the test site of the result. Furthermore, because conventional POCT readers capture, analyze and produce results at the test site, they are open to manipulation and/or doctoring.

Accordingly, there are a number of problems in the art relating to testing fluid test samples using lateral flow test, and relating to interpreting test results.

BRIEF SUMMARY OF THE INVENTION

Implementations of the present invention overcome one or more of the foregoing or other problems in the art with systems, methods, and apparatus for reading the results of drug tests while preserving the privacy of the test subject. In particular, one or more implementations allow a testing site to use generic mobile computing devices to capture one or more images a testing area of a drug test and to initiate processing of the captured image(s). In one or more implementations, general purpose mobile computing devices are enabled to image testing results from a plurality of different types of drug tests originating from a plurality of different test manufacturers. In addition, one or more implementations preserve subject privacy by enabling mobile computing devices to upload captured images to a remote server for analysis, without analyzing or storing the captured images locally. Furthermore, one or more implementations provide for a server that receives and processes drug test results, including lateral flow tests originating from a plurality of different test manufacturers.

For example, implementations of the invention may include a mobile device attachment for imaging a drug test with a mobile imaging device. The mobile device attachment includes a housing and a plurality of drug test adapters configured to removably couple to the housing. Each drug test adaptor is configured to (i) secure a corresponding type of drug test, and to (ii) align a viewing plane of the drug test with an optical viewing path within the housing. The mobile imaging device also includes one or more device nests configured to removably couple to the housing. The device nests are configured to (i) secure a corresponding type of mobile device to the housing, and (ii) optically align an imaging device of the mobile device with the optical viewing path.

In addition, implementations of the invention may also include a stationary mount for imaging a drug test with a mobile device. The stationary mount includes a pedestal. The pedestal is configured to secure one of a plurality of different types of drug tests. Each drug test includes a corresponding viewing plane that includes one or more testing result display areas. The pedestal is also configured to interface with one of a plurality of different docking stations. Each docking station is configured to secure a mobile device in a position in which an imaging device at the mobile device is optically aligned with the viewing plane of a particular drug test that is secured at the pedestal. The stationary mount also includes a particular docking station, which is selected from among the plurality of different docking stations.

Furthermore, implementations of the invention may include a server-implemented method for analyzing drug testing results from more remote testing devices in a manner that ensures privacy of a test subject. The method includes the server establishing a network communications session with a remote testing device, which is located at a geographical location that is remote from the server. The method also includes the server receiving drug testing data from the remote testing device. The drug testing data can include (i) an identification of a type drug testing apparatus being used at the remote testing device, and (ii) on or more images. The image(s) can visually represent of a portion of the drug testing apparatus being used at the remote testing device, including a test display area (such as a lateral flow test strip) of one or more drug tests. The method also includes the server identifying the type of the drug testing apparatus being used at the remote testing device, and based the identified type of the drug testing apparatus, ascertaining the results of the one or more drug tests from the image.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1E illustrates a perspective view of an interface area of a housing of a mobile device attachment system, as well as a perspective view of a corresponding interface area of a nest of a mobile device attachment system, according to one or more implementations of the invention;

FIG. 1G illustrates an interior view of a housing of a mobile device attachment system, according to one or more implementations of the invention;

DETAILED DESCRIPTION OF THE PREFERRED EMBODIMENTS

Figure 1A:
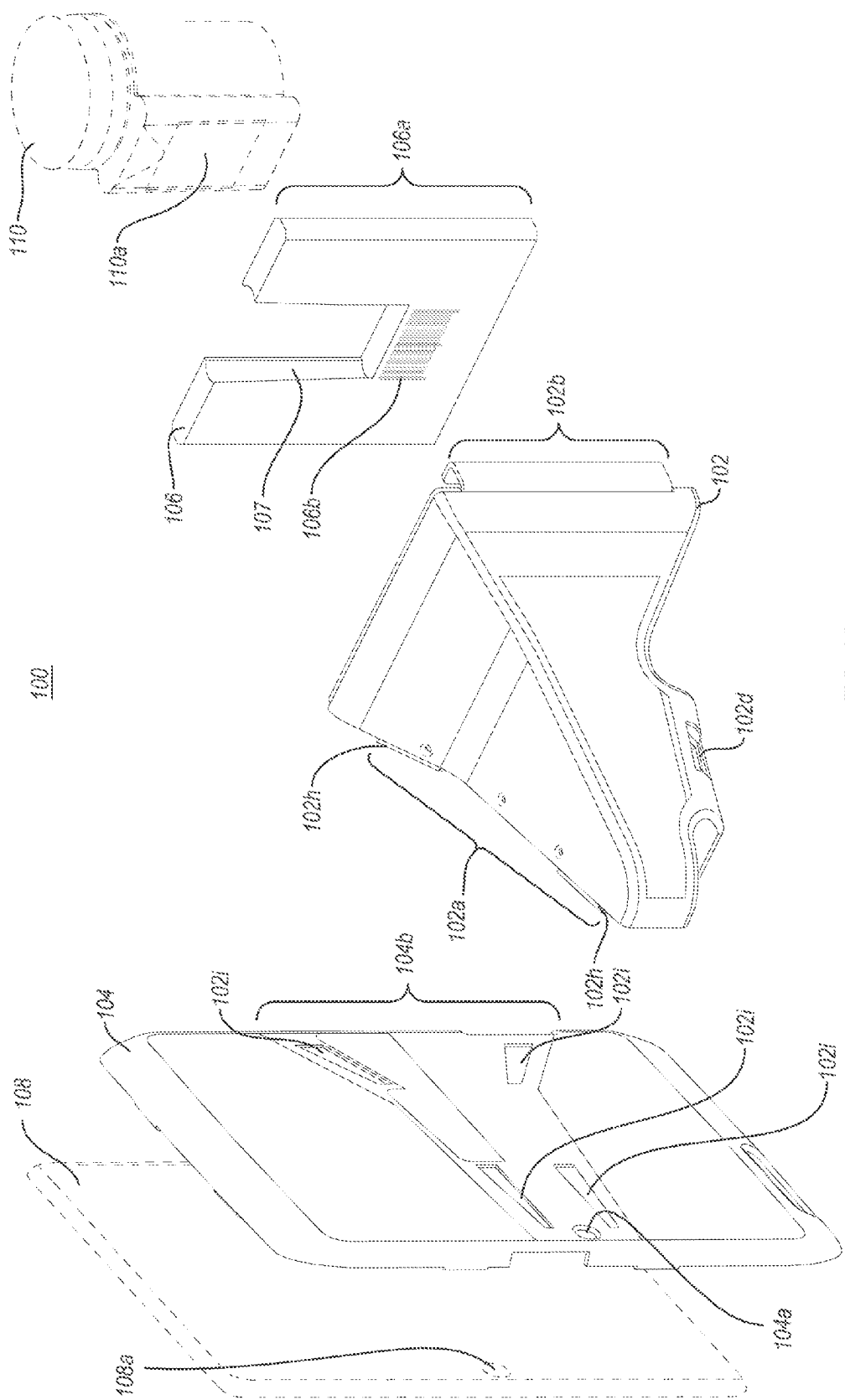
FIG. 1A illustrates an expanded perspective view of a mobile device attachment system for imaging a drug test, according to one or more implementations of the invention.

Implementations of the present invention overcome one or more of the foregoing or other problems in the art with systems, methods, and apparatus for reading the results of drug tests while preserving the privacy of the test subject. In particular, one or more implementations allow a testing site to use generic mobile computing devices to capture one or more images a testing area of a drug test and to initiate processing of the captured image(s). In one or more implementations, general purpose mobile computing devices are enabled to image testing results from a plurality of different types of drug tests originating from a plurality of different test manufacturers. In addition, one or more implementations preserve subject privacy by enabling mobile computing devices to upload captured images to a remote server for analysis, without analyzing or storing the captured images locally. Furthermore, one or more implementations provide for a server that receives and processes drug test results, including lateral flow tests originating from a plurality of different test manufacturers.

For example, at least one implementation provides a mobile device attachment housing that enables imaging of a variety of different drug tests with a mobile computing device, such as a tablet computer, a smart phone, etc. In particular, the mobile device attachment can include a device nest interface that connects the housing to a variety of different device nests. Each device nest can have a size and shape for attaching to a different type of mobile computing device. Furthermore, each device nest can have a size and shape to ensure that an imaging device on the mobile computing device is aligned to capture an image of a result viewing area of a connected drug test.

Each mobile device attachment can also include an adapter interface. The adaptor interface can have a size and shape for connecting a drug test adapter to the housing. Each drug test adapter in turn can have a size and a shape for securing a different type or brand of drug test therein. As such, the mobile device attachment housing enables testers to use off-the-shelf general purpose mobile computing devices to analyze any of a plurality of different test types from different test manufacturers. Indeed, in one or more implementations the mobile device attachment and systems of the present invention can work with any type of instant drug test and mobile computing device.

One or more other implementations provide a stationary mounting pedestal that enables a variety of different types of mobile computing devices to capture images of a variety of different types of drug tests. One or more implementations of the mounting pedestal are configured to interface with a variety of different docking stations, which each secure corresponding types of different mobile computing devices. The mounting pedestal can also interface with a variety of different types of drug tests. As such, the stationary mounting pedestal also enables testers to use off-the-shelf general purpose mobile computing devices to analyze any of a plurality of different test types from different test manufacturers.

One will appreciate that the ability to leverage the use of a mobile computing device can significantly reduce costs of a drug test reader. In addition to reducing costs of hardware needed for reading drug tests, the ability to read any type of lateral flow drug test can provide a point of testing facility with greater flexibility. Such flexibility can allow the point of testing facility performing the drug test to offer patients a wide range of drug test options.

One or more additional implementations relate to test analysis. In particular, one or more implementations enable analysis of drug tests at a location remote from a testing facility where a test subject provide a sample, thereby preserving the privacy of the test subject. These implementations can include a server, located at a first geographical location that is remote from a testing device that is located at a second, different geographical location. The server can receive the identity of a test type and an image representing a drug test result from the testing device at the second geographical location. Using this information, the server analyzes the test result. Analyzing test data at a location remote from the testing device enables the testing device to conduct testing without locally storing test results and without performing local analysis of test results. Doing so mitigates against the potential leak of sensitive information to unauthorized parties, and prevents testing personnel (who are in direct contact with the test subject) from obtaining or doctoring test results directly (when desired).

Figure 1B:
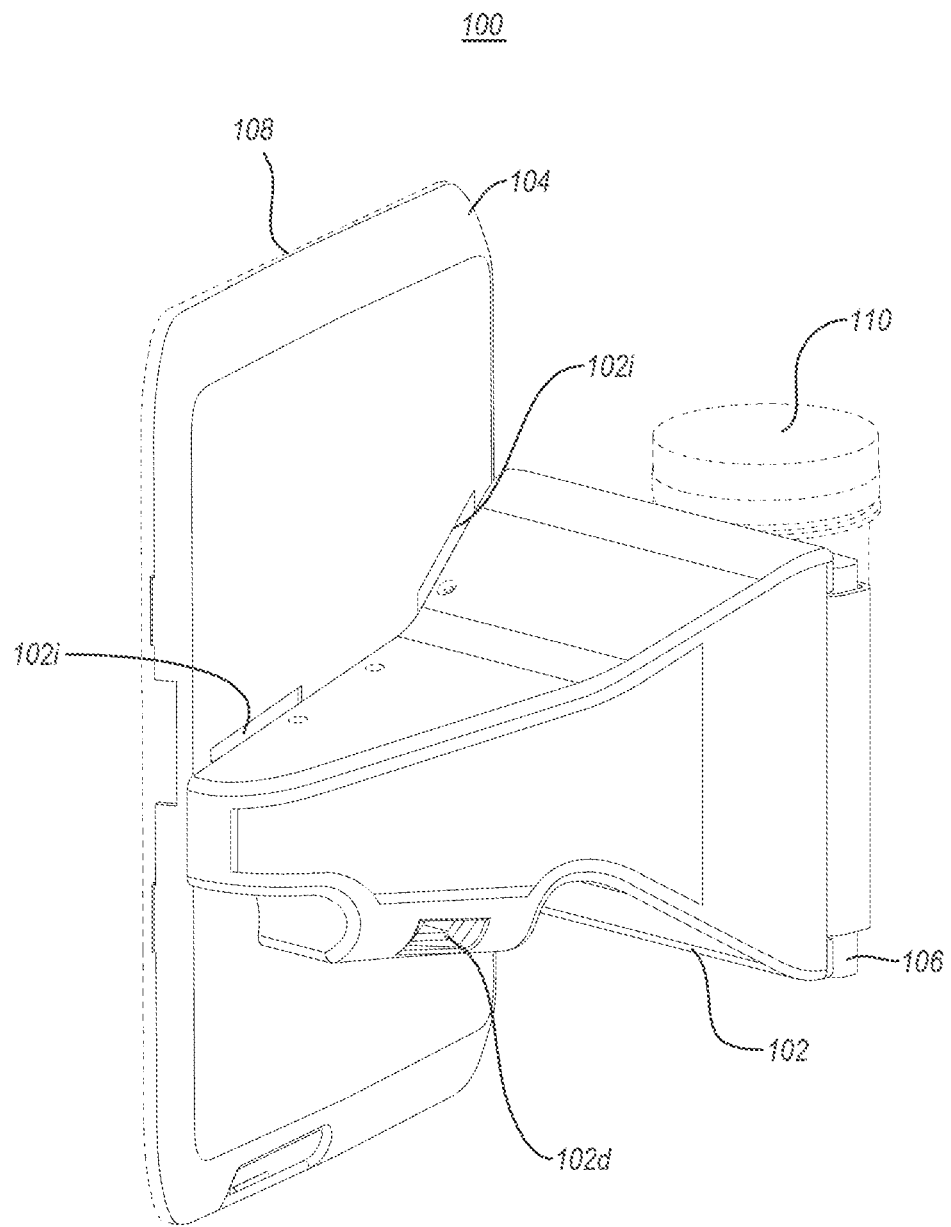
FIG. 1B illustrates an assembled perspective view of the mobile device attachment system for imaging a drug test of FIG. 1A.

Turning now to the drawings, FIG. 1A depicts an exploded perspective view of one implementation of a mobile device attachment system 100 for imaging drug tests. FIG. 1B depicts an assembled perspective view of the mobile device attachment system 100. For clarity, FIGS. 1A and 1B depict each component of the mobile device attachment system 100 using solid lines, and depict any components that are used in connection with the mobile device attachment system 100 using dashed lines. FIG. 1A depicts components of the mobile device attachment system 100 and each attached component as being spatially separated, while FIG. 1B depicts the components as being connected.

As depicted, attachment system 100 includes a housing 102, a nest 104, and a lateral flow adapter 106. Together, the housing 102, the nest 104, and the adapter 106 enable an imaging device 108a (e.g., a camera) of a mobile computing device 108 to capture one or more images of a test display area 110a of a drug test 110. In particular, the attachment system 100 aligns the imaging device 108a of the mobile computing device 108 with the test display area 110a of the drug test 110 through an optical viewing path within the housing 102.

In one or more implementations, the mobile device attachment system 100 is configured to enable a variety of different types of mobile computing devices to capture images of a variety of different types of drug tests. In particular, the mobile device attachment system 100 can include different types of nests 104 and adapters 106 that attach to the housing 102. Each different type of nest 104 interface with a particular mobile computing device (or set of mobile computing devices), and each different type of adapter 106 can interface with a particular drug test (or set of drug tests). Thus, by combining different nests 104 and different adapters 106, a single housing 102 can accommodate a broad variety of mobile computing devices and drug tests.

Figure 1C:
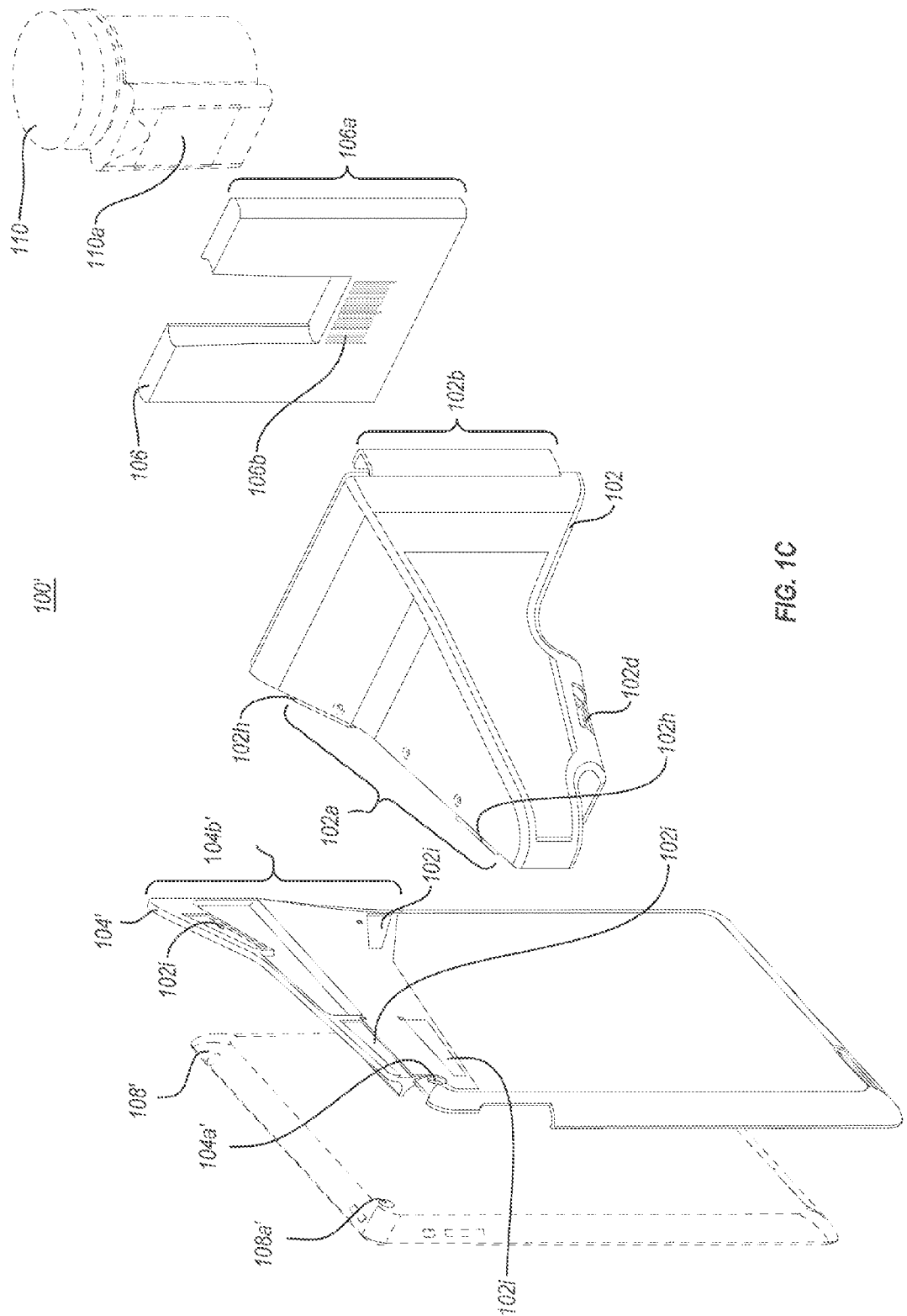
FIG. 1C illustrates an expanded perspective view of another mobile device attachment system for imaging a drug test, according to one or more implementations of the invention.
Figure 1D:
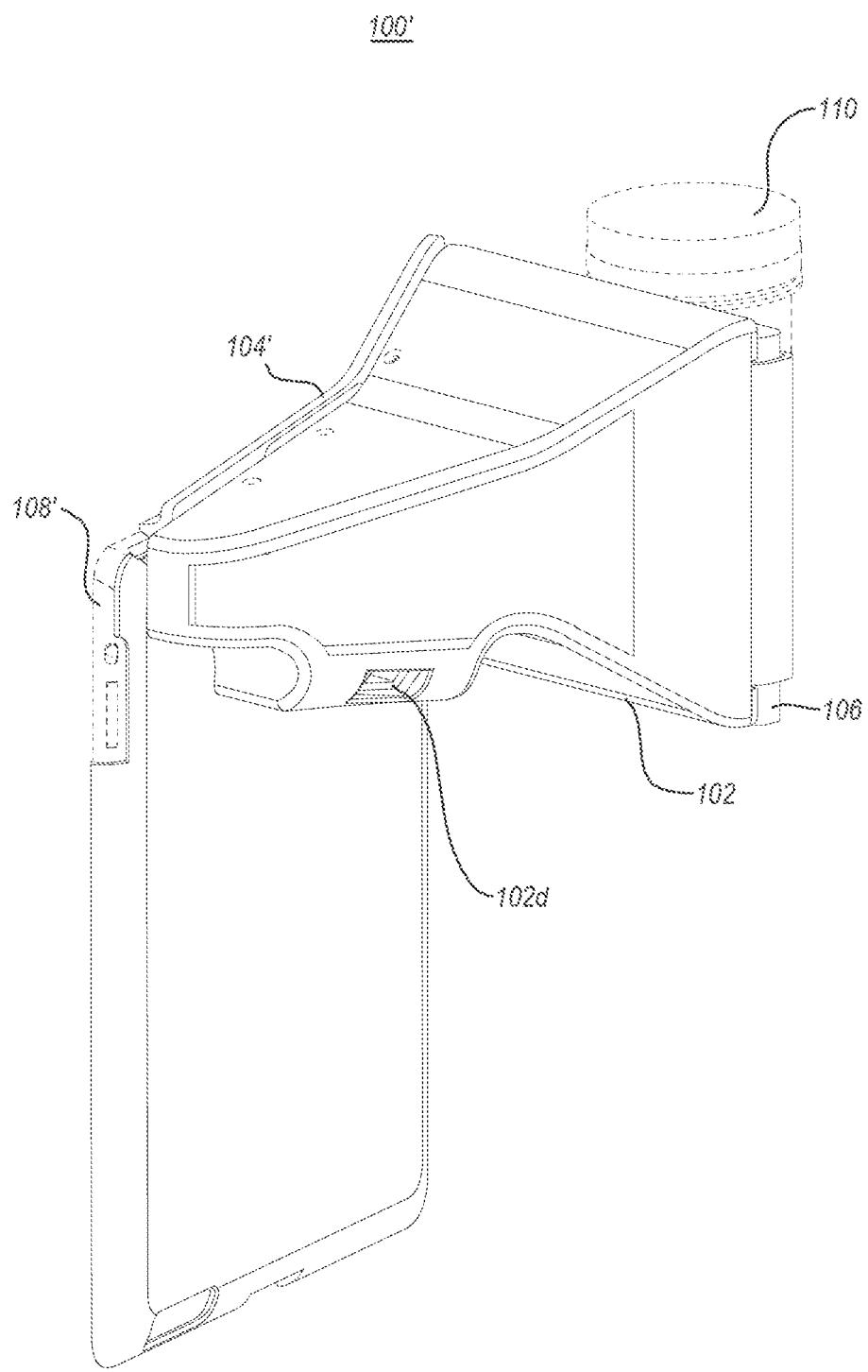
FIG. 1D illustrates an assembled perspective view of the mobile device attachment system for imaging a drug test of FIG. 1C.

FIG. 1C depicts an expanded perspective view of a mobile device attachment system 100', which includes a different type of nest 104' for attaching a different type of mobile computing device 108'. Similarly, FIG. 1D depicts an assembled perspective view the mobile device attachment system 100'. Similar to FIGS. 1A and 1B, components of the mobile device attachment system 100' are depicted using solid lines, and other component are depicted using dashed lines.

FIGS. 1A-1D depict that the different types of nests accommodate different types of mobile computing devices. For example, the nest 104 of FIGS. 1A and 1B is shown as being configured to secure a first type of mobile computing device 108 (e.g., a tablet computer from a first manufacturer). As depicted, for example, mobile computing device 108 has its imaging device 108a positioned generally at the center of a long edge. When the nest 104 attaches to the housing 102 and to the mobile computing device 108, the nest 104 is configured to align the imaging device 108a of the mobile computing device 108 with the test display area 110a via the optical viewing path (e.g., through a hole 104a in the nest 104).

Similarly, the nest 104' of FIGS. 1C and 1D is depicted as being configured to secure a second type of mobile computing device 108' (e.g., a tablet computer from a second manufacturer). As depicted, for example, mobile computing device 108' has its imaging device 108a' positioned in a corner of the device. When the nest 104' attaches to the housing 102 and to the mobile computing device 108', the nest 104' is configured to align the imaging device 108a' of the mobile computing device 108' with the optical viewing path (e.g., through hole 104a' in the nest 104').

Each nest (e.g., nests 104, 104') includes an interface area that is configured to attach with a corresponding interface area on the housing 102. For example, FIG. 1A depicts that nest 104 includes interface area 104b and FIG. 1C depicts that nest 104' includes interface area 104b'. As depicted, the interface areas 104b, 104b' may comprise one or more slots 102i. Housing 102 can include a corresponding interface area 102a. The interface area 102a of the housing 102 can include one or more tabs 102h. The tabs 102h can mate with the slots 102i of the nest 104, 104'.

For example, FIG. 1E depicts a perspective view of the interface area 102a of the housing 102, including a plurality of tabs 102h. FIG. 1E also depicts a perspective view of the interface area 104a of the nest 104, including a plurality of slots 102i that are configured to interface with the tabs 102h of interface area 102a. The tabs 102h can have a snap-fit configuration with the slots 102i. In particular, when pressed against the slots 102i, the tabs 102h can flex or otherwise deform to fit within the slots 102i. One within the slots 102i, the tabs 102h can relax back to their natural shape, thereby securing the tabs 102h within the slots 102i.

Of course, any other type of interface and/or attachment mechanism falls within the scope of the present disclosure. For example, in alternative implementations the slots 102i can comprise groove under which of portion of the tab 102h can slide to secure the housing 102 a corresponding nest 104, 104'. In still further implementation, the screws, bolts, or other fasteners can secure the housing 102 a corresponding nest 104, 104'.

Thus, one will appreciate in light of the disclosure herein that the same housing 102 can connect to any of plurality of different nests 104, 104', thereby, allowing the housing 102 to connect to any of a plurality of different mobile computing devices. One or more implementations comprises a kit that includes a single housing 102 and a plurality of different nests 104, 104'. In any event, one or more implementations allow any type of mobile computing device 108 to read a portable In addition, through use of different adapters, the housing 102 can connect to various types of drug tests. For example, a first type of adapter 106 (FIG. 1A) may secure a first type of drug test 110a (e.g., a container-style test from a first manufacturer). In particular, a groove or opening 107 in the adaptor 106 can have a size and shape corresponding to the size and shape of the test display area 110a of a given drug test 110. Thus, the groove or opening 107 in the adaptor 106 can receive and hold the drug test 110. When the first type of adapter 106 attaches to the housing 102, the first type of adapter 106 aligns the test display area 110a of the drug test 110 with the optical viewing path and with the imaging device of an attached mobile computing device.

Similarly, a second type of adapter may secure to a second type of drug test (e.g., a cassette-style test or a container-style test from a second manufacturer). For example, referring to FIG. 1F, a second type of adapter 106' may secure a second type of drug test 110 having a test display area on the lid. In particular, a groove or opening 107' in the adaptor 106' can have a size and shape corresponding to the size and shape of the lid of a given drug test 110. Thus, the groove or opening 107' in the adaptor 106' can receive and hold the lid and thus the drug test 110. When the second type of adapter 106' attaches to the housing 102, the adapter 106' aligns the test display areas of the drug test with the optical viewing path and with the imaging device of an attached mobile computing device. In some instances, different adapters may be used with different tests from the same manufacturer.

Figure 1F:
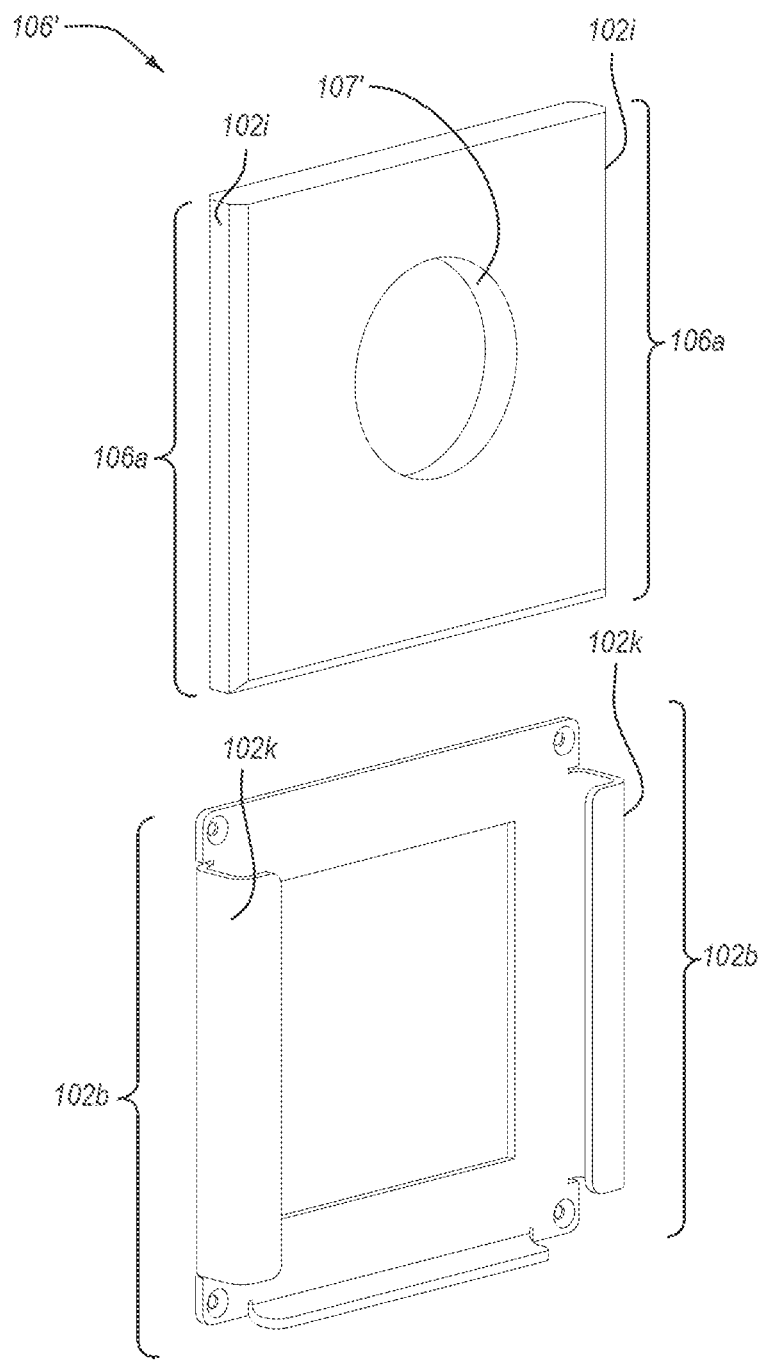
FIG. 1F illustrates a perspective view of an interface area of a housing of a mobile device attachment system, as well as a perspective view of a corresponding interface area of an adapter of a mobile device attachment system, according to one or more implementations of the invention.

Similarly, each adapter 106 includes an interface area that interfaces with a corresponding interface area on the housing 102. For example, FIGS. 1A and 1C depict that adapter 106 includes an interface area 106a, such an edge that is configured to slide into a slot 102k of a corresponding an interface area 102b on the housing 102. For example, FIG. 1F depicts a perspective view of the interface area 102b of the housing 102, including a plurality of slots 102k. FIG. 1F also depicts a perspective view of the interface area 106a of the adapter 106a, including edges 102j that are configured to slide into the slots of interface area 102b. In particular, the slots 102k comprise "L" shaped brackets sized and configured to wrap about the body of the adaptors 106, 106'. Of course, any other type of interface and/or attachment mechanism falls within the scope of the present disclosure, such screws, Velcro, snap-fit configurations, bolts, etc.

FIGS. 1A, 1C, and 1F illustrate square-shaped adaptors 106, 106'. One will appreciate that the present invention is not so limited. In alternative implementations, the adaptors can comprise circular, oval, or other shapes. In still further implementations, the adaptor can surround and hold therein a drug test 110. In other words, the adaptor can comprise a receptacle sized and shaped to hold a particular drug test 110.

In one or more implementations, each adapter 106 includes a computer-readable visual tag that identifies the adapter type and/or the drug test associated with the particular adapter 106. For example, FIG. 1A illustrates that adapter 106 includes a tag 106b. The tag 106b may include a textual description, a bar code, a QR code, or any other type of code or text that can be visually recognized and/or read by a computer system. Correspondingly, housing 102 can be configured such that, when the adapter 106 is attached to the housing, the tag 106b is included within the optical viewing field of the imaging device 108a, 108a'. As such, the imaging device 108a, can capture the tag 106b, either as part of the same image used to capture the test display area 110a, or as part of a different image. Then, by reading the visual tag 106b, a computer system that processes images captured by the imaging device 108a, 108a' can recognize the type of drug test that is being used, and process the visual results of the test accordingly.

One will appreciate in light of the disclosure herein that in alternative implementations the tag 106b can reside on the drug test 110, the test display area 110a, or another portion of the mobile device attachment system 100. In yet additional implementations, the information that identifies the type of drug test can reside on both the adaptor 106 and the drug test 110. For example, the information can be duplicated or split between one or more of the adaptor 106, the drug test 110, the test display area 110a, or another portion of the mobile device attachment system 100. Alternatively, the tag 106b comprise a label that a user can place as desired.

In still further implementations, the mobile device attachment system 100 includes no tag 106b. In such implementations the software program can prompt the user for information, such as the type of drug test. Then using the provided information, the computer system that processes images captured by the imaging device 108a, 108a' can recognize the type of drug test that is being used, and process the visual results of the test accordingly.

The housing 102 may provide for controlled lighting conditions for the imaging device 108a, 108a' to capture one or more images of the test display area 110a. For example, FIG. 1G illustrates an internal view of the housing 102. As depicted, the housing 102 can block all, or substantially all, ambient light, and provide a variety of mechanisms to ensure consistent image quality.

In one or more implementations, the housing 102 may include an illumination device 102c (or a plurality of devices). The illumination device(s) 102c can provide lighting to an imaging plane of the housing 102 at a consistent intensity and color temperature (white balance). For example, FIG. 1G depicts that the illumination device 102c may comprise a lighting array, such a square or circular LED lighting array. Of course other types of illumination devices can be used having various shapes, number of illuminators, and illumination technology (e.g., incandescent), etc.

As shown by FIG. 1G, in one or more implementations the LED lighting array can completely surround the test display area 110a and the tag 206b. In alternative implementations, the LED lighting array can extend along one or more of the sides of the test display area 110a and the tag 206b. In still further implementations, the illumination device is positioned on the housing 102 opposite the test display area 110a and the tag 206b.

In any event, in one or more implementations the illumination device 102c comprises a plurality of LED lights. As shown by FIG. 1G, in one or more implementations each LED light is equally spaced from adjacent LED lights along each respective edge. Furthermore, FIG. 1G illustrates that each corner of the illumination device 102c can comprise an LED light at the each end of each side (left, right, top, and bottom). Having two LED lights at each corner can help reduce hot spots or other uneven lighting.

In one or more implementations, the housing 102 includes one or more mirrors. For example, FIG. 1G depicts that the housing 102 includes a mirror 102e that is configured to optically align an imaging device 108a, 108a' of an attached mobile computing device with a test display area 110a of an attached drug test. For example, the mirror 102e may be positioned at, or approximately at, a 45° angle relative to an imaging device 108a, 108a' to align the imaging device 108a, 108a' with the optical viewing path through the housing 102. Thus, one will appreciate that in one or more implementations the mirror 102e is aligned with the hole 104a of the respective nest 104, 104'.

In addition, one or more implementations of the housing 102 include one or more reflectors or reflective surfaces. For example, the FIG. 1G depicts that the housing 102 can include a plurality of reflectors 102g surrounding the illumination device 102c. The reflectors 102g can reflect light generated by the illumination device 102c back to the imaging plane, ensuring that the test display area 110a is illuminated consistently. For example, in one more implementations the reflectors 102g are oriented at approximately 45 degrees relative to the test display area 110a. The reflectors 102g can help ensure that the entire test display area 110a is evenly lit.

Furthermore, one or more implementations of the housing 102 include one or more visual calibration cues (not shown). The calibration cues are configured to provide a known visual metric (e.g., shade of color), which can be used by a computer system processing images captured using the housing 102 to adjust image parameters (e.g., brightness, contrast, saturation, etc.) so that the known visual metric is accurately reproduced in the captured images. Doing so can more accurately reproduces colors of drug test results, thereby improving test accuracy.

In implementations in which the housing 102 includes an illumination device 102c, the housing 102 may also include components that are configured to control and/or power the illumination device 102c. For example, FIGS. 1A-1D depict that the housing 102 can include a power actuator 102d (e.g., a button or switch). In addition, the housing 102 may include one or more batteries, one or more solar cells, or any other type of power generation or storage device. In particular, as shown by FIG. 1G, the housing 102 can include a battery compartment positioned below the mirror 102e. In one or more implementations, the housing 102 may derive electrical power from the attached mobile computing device 108, such as through a cable that connects to an electrical or data port on the device.

FIGS. 1A-1G illustrate that the housing 102 comprises a generally narrow portion near the mirror 102e that increases in size as it extends toward the illumination device 102c. One will appreciate that the present invention is not so limited. In alternative implementations the housing 102 can comprise any number of different shapes and configurations.

Figure 2A:
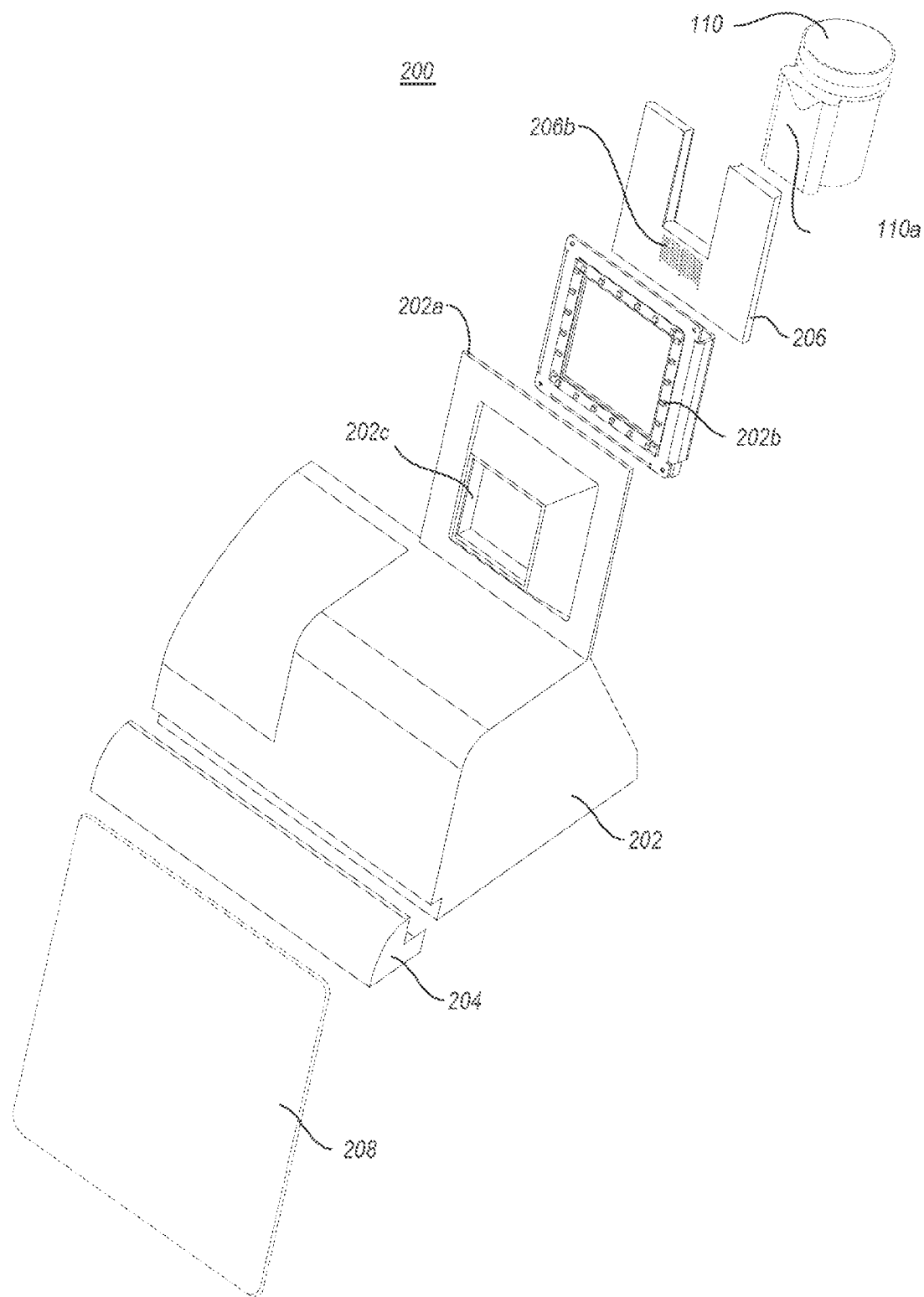
FIG. 2A illustrates an exploded perspective view of a stationary mount for imaging a drug test, according to one or more implementations of the invention.
Figure 2B:
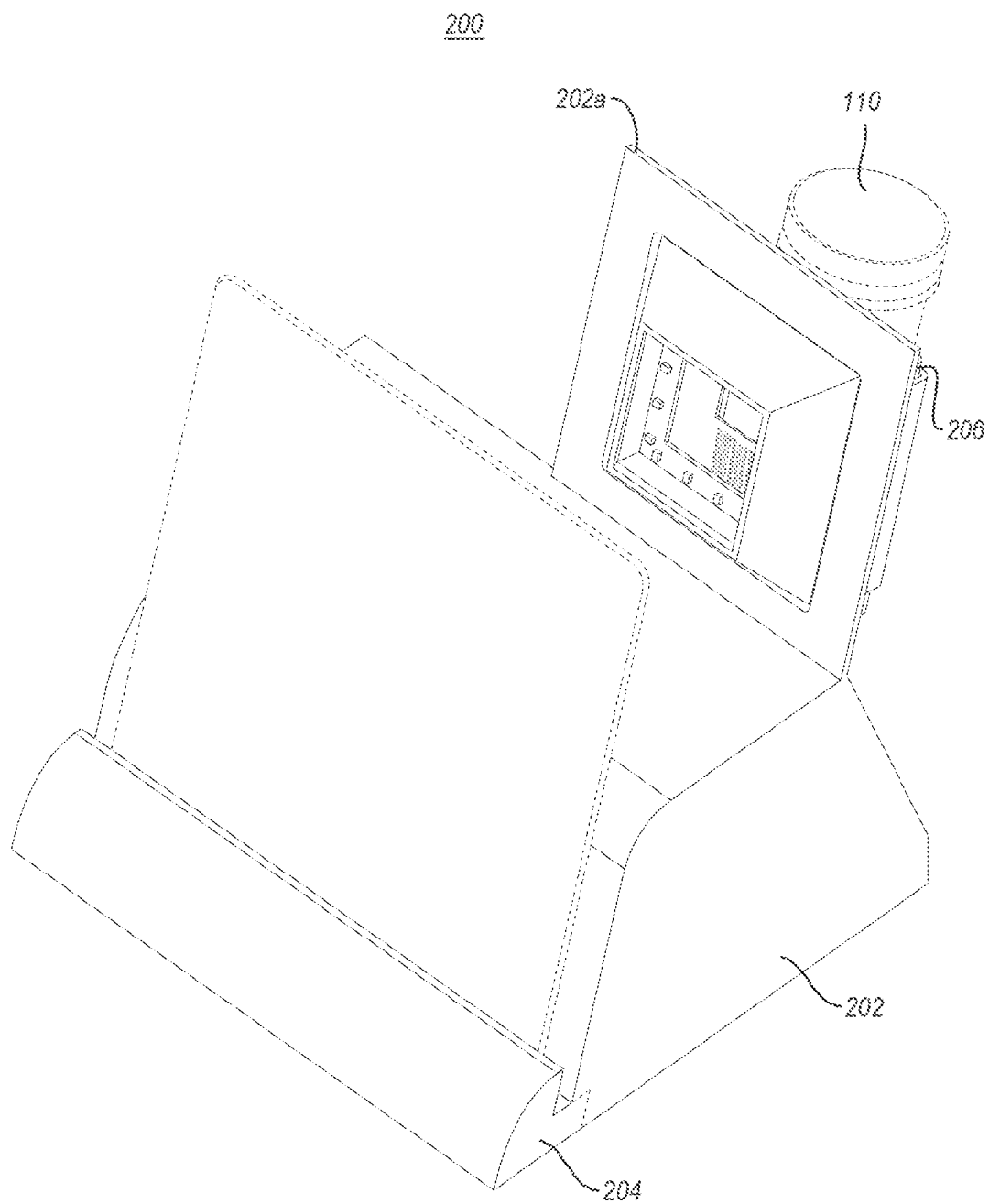
FIG. 2B illustrates an assembled perspective view of the stationary mount for imaging a drug test of FIG. 2A.

Furthermore, one or more implementations of the invention can take a number of forms beyond the mobile device attachment systems 100, 100' shown and described in relation to FIGS. 1A-1G. For example, FIG. 2A depicts an exploded perspective view of a stationary mount system 200 for imaging drug tests, and FIG. 2B depicts an assembled perspective view of the stationary mount 200. Similar to FIGS. 1A-1D, components of stationary mount system 200, itself, are depicted using solid lines, while other related components are depicted using dashed lines. As depicted, the stationary mount system 200 includes a pedestal 202 (i.e., a type of housing), a dock 204 (i.e., a type of nest), and an adapter 206.

The pedestal 202 is configured to interface with one of a plurality of different docks 204. Each different dock 204 is configured to secure a different type of mobile computing device 208, and to align an imaging device of the mobile computing device 208 with an imaging area 202a of the pedestal 202. The pedestal 202 is also configured to interface with one of a plurality of different adapters 206. Each adapter 206 is configured to secure a different type of drug test 210, and to align a test display areas 210a of the drug test 210 with the imaging area 202a. As such, similar to the housing 102 of the mobile device attachment system 100, 100', the pedestal 202 is configured to enable a variety of different mobile computing devices to be used to image a variety of different drug tests.

Like the adapters 106 of the mobile device attachment system 100, 100', each adapter 206 may include a computer-readable visual tag 206b (e.g., bar code, QR code, etc.). The tag 206b can identify the particular adapter that is being used, and enables a computer system that processes images captured using the stationary mount system 200 to identify the type of drug test that is being imaged. As such, as depicted, the imaging area 202a can enable an imaging device to capture a portion of the adapter 206 containing the tag 206a.

The imaging area 202a can include one or more components that are configured to provide optimized lighting conditions for capturing images of drug tests. For example, the imaging area 202a can include an illumination device 202b (or devices), such as the depicted LED lighting array, and one or more reflectors 202c or reflective surfaces. The illumination device 202b may be configured to provide lighting at a particular intensity and color temperature, and the reflectors 202c may be configured to reflect light emitted from the illumination device 202b in a manner that provides consistent illumination within the imaging area 202a. In addition, the imaging area 202a may include one or more calibration cues, such as one or more known colors that can be used to adjust image parameters of captured images.

While mobile device attachment system 100 and stationary mount system 200 have been described as being used with mobile computing devices such as tablet computers, smart phones, etc., these systems may, in some implementations, be adapted to be used with a broad range of devices, such as stand-alone or peripheral imaging devices (e.g., digital cameras, web-cams, etc), laptop or desktop computers, etc. For example, mobile device attachment system 100 may include a nest 104 that is adapted to attach to a webcam on a laptop computer, or to connect to a peripheral webcam directly. In another example, stationary mount system 200 may include a dock 204 that is adapted to secure a standalone camera. As such, a broad range of configurations are within the scope of the present disclosure.

Figure 3:
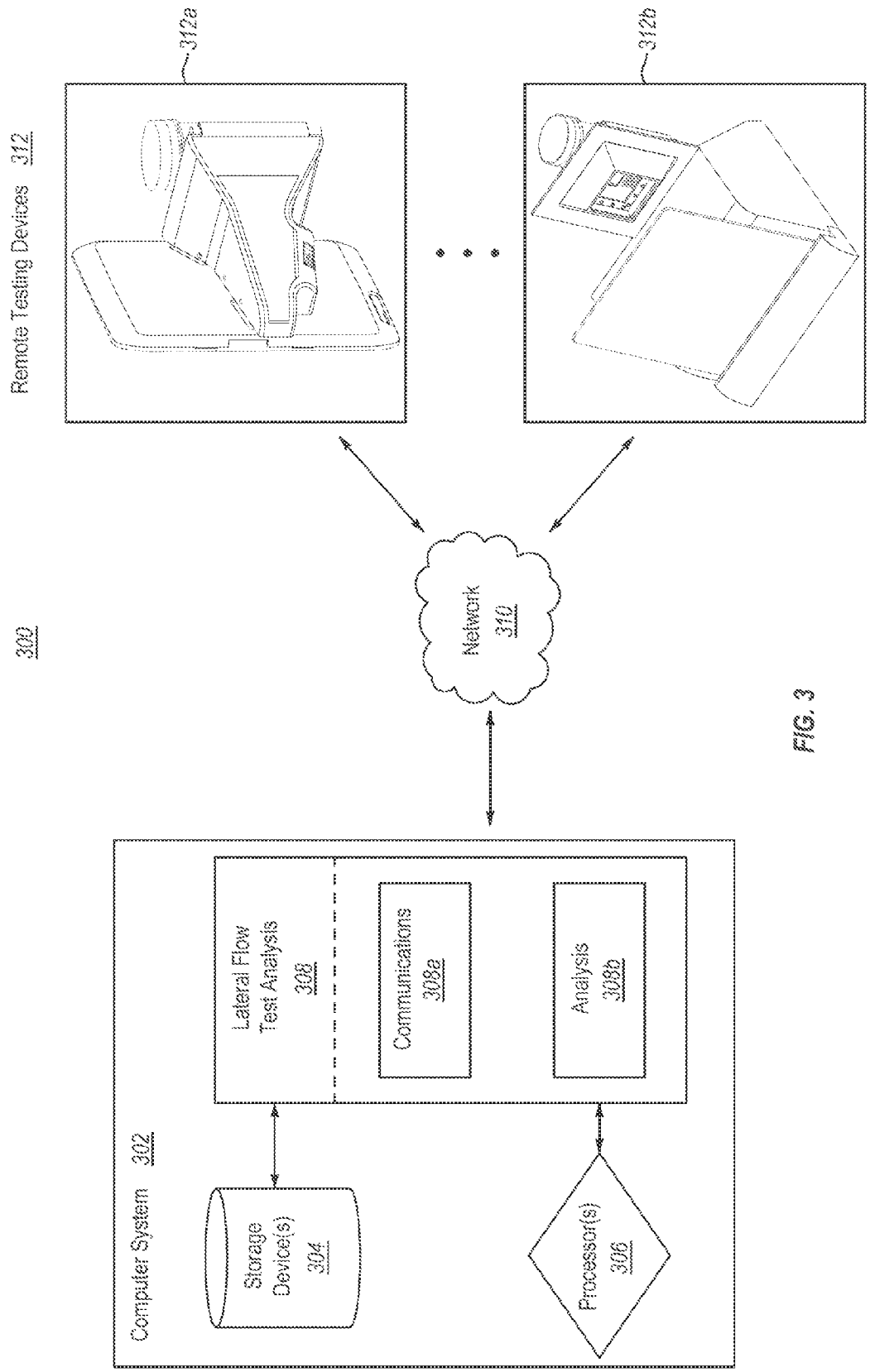
FIG. 3 illustrates a computer architecture for processing drug tests, according to one or more implementations of the invention.

Implementations of the invention include one or more computer architectures for processing results of drug tests. One or more implementations preserve the privacy of individuals whose biological fluids or tissues are being tested by processing the test results at a location remote from the testing. FIG. 3, for example, depicts computer architecture 300 for processing drug tests according to one or more implementations of the invention.

As depicted, computer architecture 300 includes a computer system 302 (e.g., a server computer system) and one or more remote testing devices 312 that are remotely connected to the computer system 302 over a network 310. Each of the remote testing devices 312 can comprise an appropriate device (e.g., camera, mobile computing device, laptop or desktop computer) that is connected to a mobile device attachment system 100 or a stationary mount system 200. For example, FIG. 3 depicts that the remote testing devices 312 may include a remote testing device 312a, which comprises a mobile computing device connected to the mobile device attachment system 100, and a remote testing device 312b, which comprises a mobile computing device connected to a stationary mount system 200.

The computer system 302 includes one or more processors 306, one or more storage devices 304, and a drug test analysis component 308. The drug test analysis component 308 may comprise a software application or module executing on the one or more processors 306. The storage device(s) 304 may store data used or produced by the drug test analysis component 308. As depicted, the drug test analysis component 308 includes a communications module 308a and an analysis module 308b.

The communications module 308a is configured to establish one or more communications sessions with the remote testing devices 312 and to receive data relating to drug test from the remote testing devices 312. In particular, the communications module 308a is configured to receive data identifying the type of drug test being performed at a remote testing device 312, and one or more images representing a test display areas of a drug test.

The data identifying the type of drug test may identify a particular type of adapter being used at a remote testing device 312a. For example, the data identifying the type of drug test may comprise a computer-readable visual tag 106a that is captured from the adapter 106 being used. In another implementation, the data identifying the type of drug test may comprise may comprise a code or text string received from the remote testing device 312a. Of course, the data identifying the type of drug test may come in any other appropriate form.

The one or more images representing a test display areas of a drug test may comprise one or more images captured at the remote testing device 312a, 312b. For example, the image(s) may visually represent all or part of testing result display area 110a. The one or more images may also include one or more color calibration cues. The one or more images may also include the data identifying the type of drug test. For example, a single image may include both a test display areas of a drug test and a computer-readable visual tag from an adapter.

The analysis module 308b is configured to process data related to drug tests that is received by communications module 308a. In particular, analysis module 308b can ascertain testing results from the received data. For example, the analysis module 308b can ascertain the identification of the test being performed through analysis of one or more images comprising a computer-readable visual tag, or through any other appropriate mechanism. The analysis module 308b may also process the one or more images representing testing results to ascertain the testing result.

Analysis module 308b is configured to retrieve and/or store data in storage device(s) 304. For example, analysis module 308b can retrieve instructions for interpreting test results for a particular test based on the identification of the test being performed. Analysis module 308b may store testing results in storage device(s) 304 and/or to send testing results back to a remote testing device 312 or to another computer system.

Figure 4:
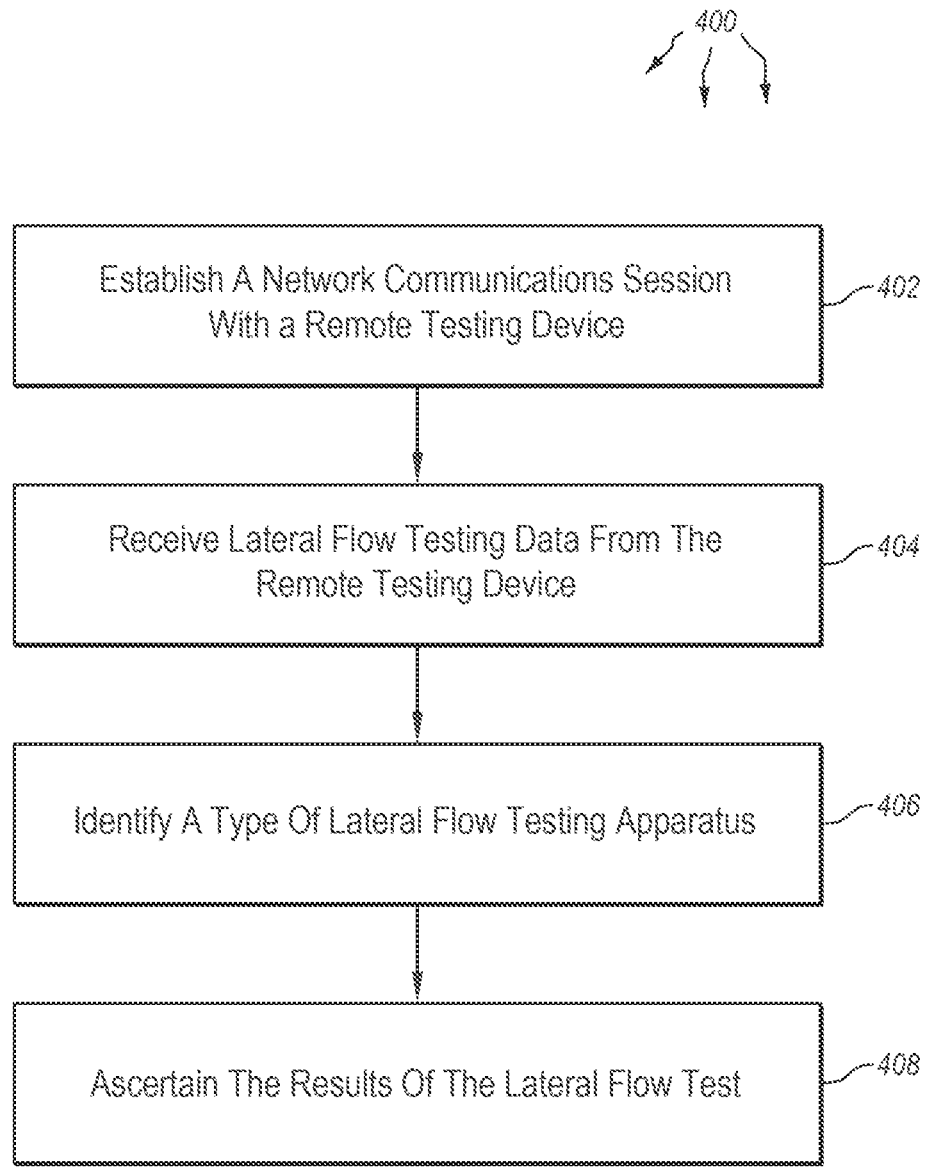
FIG. 4 illustrates a flowchart of a method for analyzing drug testing results from a remote testing device in a manner that ensures privacy of a test subject, according to one or more implementations of the invention.

FIG. 3 provides a computer architecture for processing drug tests. In addition to the foregoing, implementations of the present invention can also be described in terms of flowcharts comprising one or more acts in a method for accomplishing a particular result. For example, FIG. 4 illustrates a method 400 of analyzing drug testing results from remote testing devices in a manner that ensures privacy of a test subject. The acts of FIG. 4 are discussed more fully below with respect to schematics of FIG. 3. Of course, as a preliminary manner, one of ordinary skill in the art will recognize that the methods explained in detail herein can be modified.

For example various acts of each method described can be omitted or expanded, and the order of the various acts of each method described can be altered as desired.

For example, FIG. 4 shows that the method 400 of analyzing drug testing results from remote testing devices in a manner that ensures privacy of a test subject can comprise an act 402 of establishing a network communications session with a remote testing device. Act 402 can include establishing a network communications session with a remote testing device, the remote testing device being located at a remote geographical location. For example, communications module 308a can establish a network communications session with the remote testing device 312a. As depicted, remote testing device 312a may comprise a mobile computing device (e.g., smart phone, tablet computer) that is operating in connection with the mobile device attachment system 100. The remote testing device 312a may be located at a geographical location that is remote from computer system 302, such as at a place of employment, lab, prison, school, etc.

In addition, FIG. 4 shows that the method 400 in accordance with an implementation of the present invention can comprise an act 404 of receiving drug testing data from the remote testing device. Act 404 can include receiving drug testing data from the remote testing device, the drug testing data including (i) an identification of a type drug testing apparatus being used at the remote testing device, and (ii) an image, the image comprising a visual representation of a portion of the drug testing apparatus being used at the remote testing device, which includes a visual result of one or more drug tests. For example, communications module 308a can receive one or more images captured by the mobile computing device that is attached to the mobile device attachment system 100. The image can include the test display area 110a. The image may also include tag 106b, which identifies adapter 106. In one or more implementations, however, the identification of the adapter 106 may be sent as a code or text string generated by the mobile computing device upon the mobile computing device recognizing the tag 106b.

In any event in one or more implementations, the remote testing device 312 captures and sends only image data (i.e., one or more images of the test display area 110a and/or tag 106b) and does not send a test result. In other words, the remote testing device 312 does not analyze the test display area 110a for the presence of, or lack of, lines or colors from the drug test. Nor does the remote testing device 312 interpret the presence of, or lack of, lines or colors to determine the presence or lack of a drug or condition in the test sample. One will appreciate in light of the disclosure herein that by avoiding having the test result determined at the testing site (whether by the remote testing device 312 or otherwise), the integrity, accuracy, and privacy of the test can be maintained.

FIG. 4 also shows that the method 400 in accordance with an implementation of the present invention can comprise an act 406 of identifying a type of drug testing apparatus. Act 406 can include identifying the type of the drug testing apparatus being used at the remote testing device. In particular, the analysis module 308b can read the tag 106b including in image data received from the remote testing device 312 via the network 310. Based on the received identification of a type drug testing apparatus, the analysis module 308b at the remote computer system 302 can consult adapter or test data stored on the storage device(s) 304. For example, the storage device(s) 304 may include data that maps tags or identification codes to drug test types.

Furthermore, FIG. 4 shows that the method 400 in accordance with an implementation of the present invention can comprise an act 408 of ascertaining the results of the drug test.

Act 408 can include, based the type of the drug testing apparatus being used at the remote testing device, ascertaining the results of the one or more drug tests from the image. For example, based on data obtained from storage device(s) 304, the analysis module 308b can interpret the visual results of the drug test(s) represented in the received image(s).

For example, act 408 can comprise analyzing certain areas of the image of the test display area 110a received from the remote testing device 312 via the network 310 for the presence or lack of lines, colors, or other indicia. Act 408 can then involve interpreting the presence or lack of lines, colors, or other indicia to determine a test result (i.e., presence of a drug or condition). Thus, the test result is determined at the computer system 302 that is remote from the test site. As mentioned previously, determining the test result at a location physically remote from the testing site can help prevent the inadvertent dissemination of the test result, and allow for quality control over the interpretation of the test.

Although not depicted, method 400 can include one or more additional acts. For example, method 400 can include acts of adjusting the received one or more images based on color calibration data included in the images, associating the results of the drug test with the network communications session, storing the test results, sending the test results to another computer system, etc. In still further implementations, the method 400 can comprise entering data about one or more of the test subject, the type of test, or other information to associate the particular test subject with the particular network communications session.

Implementations of the present invention may comprise or utilize a special purpose or general-purpose computer including computer hardware, such as, for example, one or more processors and system memory, as discussed in greater detail below. Implementations within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the invention can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A computerized method, implemented at a server computer system that includes one or more processors and that is connected to one or more remote testing devices via one or more network connections, the computerized method for analyzing drug testing results from the one or more remote testing devices in a manner that ensures privacy of a test subject, the method comprising acts of:
    establishing a network communications session with a remote testing device, the remote testing device being located at a remote geographical location;

receiving drug testing data at the server computer system from the remote testing device, the drug testing data including:
  an identification of a type of drug testing apparatus being used at the remote testing device; and
  an image, the image comprising a visual representation of at least a portion of the drug testing apparatus being used at the remote testing device;
identifying the type of the drug testing apparatus being used at the remote testing device based on the portion of drug testing apparatus that was visually represented in the image; and
ascertaining, at the server computer system, the results of the one or more drug tests from the image received from the remote testing device based the type of the drug testing apparatus being used at the remote testing device.

2. The method of claim 1, wherein:
the image includes the identification of the type of the drug testing apparatus being used at the remote testing device, and
  identifying the type of the drug testing apparatus being used at the remote testing device comprises an act of analyzing the image to identify the type of the drug testing apparatus being used at the remote testing device.

3. The method of claim 2, wherein the act of analyzing the image to identify the type of the drug testing apparatus being used at the remote testing device comprises an act of analyzing a computer-readable visual tag contained in the image.

4. The method of claim 1, further comprising associating the results of the one or more drug tests with the network communications session.

5. The method of claim 1, wherein ascertaining the results of the one or more drug tests from the image comprises recognizing one or both of presence of a line or color or a lack of a line or color on the visual results of one or more drug tests.

6. The method of claim 5, wherein recognizing one or both of presence of a line or color or a lack of a line or color on the visual results of one or more drug tests is based on the identified the type of the drug testing apparatus.

7. The method of claim 1, wherein ascertaining, at the server computer system, the results of the one or more drug tests from the image comprises reading a lateral flow test.

8. A computerized method, implemented in a system comprising a remote testing device and a second computer system, the remote testing device and second computer system each including one or more processors and each being connected to one or more server computer systems via one or more network connections, the computerized method for analyzing drug testing results from the one or more remote testing devices and second computer system in a manner that ensures privacy of a test subject, the method comprising acts of:
  establishing a network communications session with a server computer systems, the server computer system being located at a remote geographical location;
  sending drug testing data to the server computer system from the remote testing device, the drug testing data including:
    an identification of a type of drug testing apparatus being used at the remote testing device; and
    an image, the image comprising a visual representation of at least a portion of the drug testing apparatus being used at the remote testing device, the image allowing the type of the drug testing apparatus to be determined based on the portion of the drug testing apparatus that was visually represented in the image;
  the second computer system establishing a second network communications session with the server computer system; and
  receiving at the second computer system from the server computer system, the results of the one or more drug tests from the image received from the remote testing device based the type of the drug testing apparatus being used at the remote testing device.

* * * * *